United States Patent
Li et al.

(10) Patent No.: US 9,295,446 B2
(45) Date of Patent: Mar. 29, 2016

(54) METHODS AND SYSTEMS FOR PULSE SCANNING AND SIMULTANEOUSLY DISPLAYING A BLOOD FLOW IMAGE AND A B-MODE IMAGE

(75) Inventors: Lei Li, Shenzhen (CN); Yongqiang Dong, Shenzhen (CN)

(73) Assignee: SHENZHEN MINDRAY BIO-MEDICAL ELECTRONICS CO., LTD, Shenzhen (CN)

( * ) Notice: Subject to any disclaimer, the term of this patent is extended or adjusted under 35 U.S.C. 154(b) by 411 days.

(21) Appl. No.: 13/102,456

(22) Filed: May 6, 2011

(65) Prior Publication Data

US 2012/0029350 A1  Feb. 2, 2012

(30) Foreign Application Priority Data

Jul. 29, 2010 (CN) .......................... 2010 1 0245596

(51) Int. Cl.
*A61B 8/06* (2006.01)
*A61B 8/08* (2006.01)

(52) U.S. Cl.
CPC ................. *A61B 8/06* (2013.01); *A61B 8/5238* (2013.01)

(58) Field of Classification Search
CPC ............................ A61B 8/5238; A61B 8/5246
USPC .................................................. 600/437, 440
See application file for complete search history.

(56) References Cited

U.S. PATENT DOCUMENTS

| | | | |
|---|---|---|---|
| 5,438,995 A * | 8/1995 | Washburn et al. | 600/447 |
| 5,718,229 A | 2/1998 | Pesque et al. | |
| 6,139,501 A | 10/2000 | Roundhill et al. | |
| 6,450,961 B1 | 9/2002 | Shiki et al. | |
| 7,775,981 B1 * | 8/2010 | Guracar et al. | 600/447 |
| 2005/0228282 A1 | 10/2005 | Wang et al. | |
| 2007/0073152 A1 * | 3/2007 | Washburn | 600/441 |
| 2009/0192387 A1 | 7/2009 | Yao | |
| 2011/0208056 A1 * | 8/2011 | Datta et al. | 600/441 |

FOREIGN PATENT DOCUMENTS

| | | |
|---|---|---|
| CN | 1257695 A | 6/2000 |
| CN | 1682664 A | 10/2005 |
| CN | 201160859 Y | 12/2008 |
| EP | 1 826 587 A2 | 8/2007 |
| EP | 2063228 A2 | 5/2009 |

* cited by examiner

*Primary Examiner* — Rochelle Turchen
(74) *Attorney, Agent, or Firm* — Kory D. Christensen; Stoel Rives LLP

(57) ABSTRACT

Methods and systems for pulse scanning and simultaneously displaying a blood flow image and a B-mode image are disclosed.

4 Claims, 5 Drawing Sheets

METHODS AND SYSTEMS FOR PULSE SCANNING AND SIMULTANEOUSLY DISPLAYING A BLOOD FLOW IMAGE AND A B-MODE IMAGE

CROSS-REFERENCE TO RELATED APPLICATION(S)

This application claims the benefit of Chinese Patent Application No. 201010245596.3, filed on Jul. 29, 2010, which is incorporated herein by reference in its entirety.

TECHNICAL FIELD

The following disclosure relates to medical ultrasonic imaging.

SUMMARY OF THE INVENTION

Disclosed herein are methods and systems for pulse scanning and simultaneously displaying a blood flow image and a B-mode image.

DETAILED DESCRIPTION

Medical ultrasonic imaging equipment acquires ultrasonic characteristic information of human tissues and organs by ultrasonic propagation in a human body. In existing ultrasonic imaging systems, a probe with multiple array elements is usually used, and a high-voltage pulse wave is loaded on each of the array elements of the probe to excite the array elements to generate high-frequency ultrasonic waves to form a transmission wave beam to enter a human body. Each of the array elements of the probe receives echoes scattered or reflected by human tissues, which forms a reception wave beam. Information extracted from the echoes (or the reception wave beam) are then used to form images for displaying according to different modes.

A transmission and reception module sends echo signals to a beamformer module for processing to increase a signal to noise ratio (SNR) of the echo signal. An output signal of the beamformer module is sent to a corresponding signal processing module according to the properties of the echo signal. Signals or information related to a B-mode image are sent to a two-dimensional B-mode signal processing module to acquire two-dimensional B-mode image data. Signals or information related to a color blood flow are sent to a color blood flow signal processing module to acquire color blood flow image data. Finally, the B-mode image data and the color blood flow data are combined by a display module to form result data to be simultaneously displayed on a monitor.

A color blood flow image mode (Color mode) refers to a mode in which dynamic information of blood cells in a blood flow is calculated according to a target display method. Primary colors of red, blue, and green are mixed and the brightness thereof varies according to a moving direction, a speed, and a dispersion situation of the blood cells, which are superimposed on a two-dimensional scan image (a B-mode image).

Figure 1:
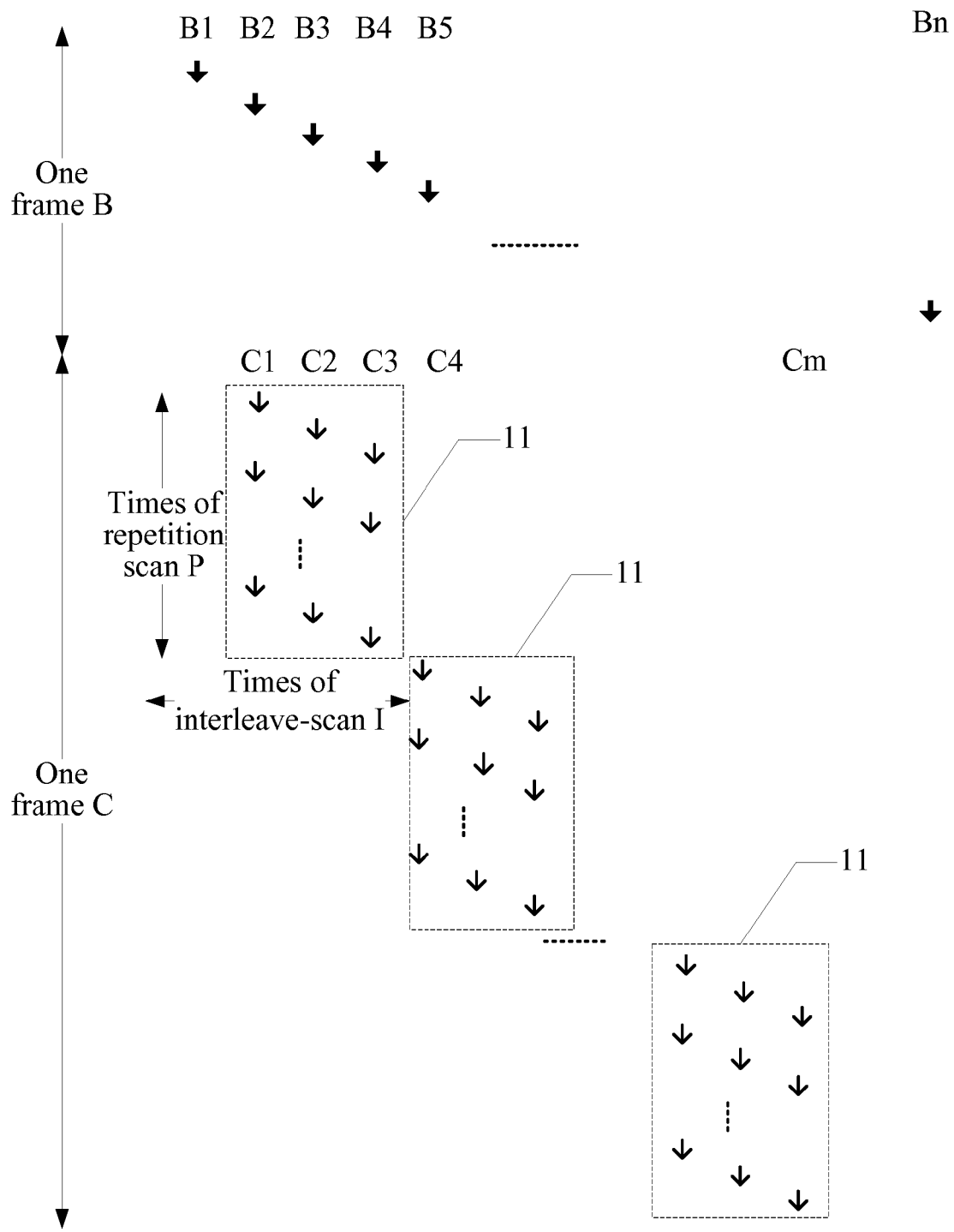
FIG. 1 is a schematic view of a scanning method for simultaneously displaying a continuous blood flow image and a B-mode image in an ultrasonic system.

According to a typical scanning method in the art, a frame C (a frame of a Color mode scan) and a frame B (a frame of a B-mode scan) are alternately transmitted. As shown in FIG. 1, a system first scans a frame B, then a frame C, then a frame B, then a frame C, and so on in a repeated manner. The B-mode scan is represented by a symbol "↓" in FIG. 1, and the Color scan is represented by a symbol "↓". The Color scan is performed in an interleave-scanning mode to increase scan efficiency to increase a frame rate. Scanning of a frame B is performed on each of B-mode scan lines (B1, B2, ..., Bn) successively from left to right in a scan range. A frame of the Color scan includes multiple Color scan groups, each of the groups includes multiple scan lines (C1, C2, ..., Cm), each frame of Color scan divides an entire scan range into several Color interleave-scan packets 11, and each of the interleave-scan packets 11 has I*P Color scan lines. I is the number of times (InterNum) of the interleave-scanning, and is determined by the pulse repetition frequency of the Color scan and a sampling depth D. P is the repeat scanning times (Packet-size) of the Color signal, and is be predetermined by the ultrasonic imaging system.

Unfortunately, the scanning method mentioned above has a low frame rate. Also, when the color blood flow signal is processed by a wall filter for filtering the noise from relatively static tissue, the quality of wall filtering is decreased, as the Color scan lines between two frames are not continuous. Therefore, it can affect the quality of the ultrasonic images.

The present disclosure is directed to a systems and methods for pulse scanning and for simultaneously displaying a blood flow image and a B-mode image so as to shorten time required for scanning and decrease a time interval between adjacent Color scan lines at the same location.

In one aspect, a pulse scanning method is provided, in which scanning of an entire color blood flow image is completed through an interleave-scan packet. The interleave-scan packet includes at least one scan group, each of the scan groups uses a pulse repetition period of the color blood flow image scanning as a unit scanning time, and within each unit scanning time, a part of the time is used for the color blood flow image scanning, and a part of the time is used for scanning of a B-mode image.

In the pulse scanning method, each of the scan groups includes a group of complete color blood flow image scan lines and at least one B-mode scan line, all of the B-mode scan lines in each of the scan groups form a frame of complete B-mode scan lines, and a group of color blood flow image scan lines in each of the scan groups form a frame of complete color blood flow image scan lines. A time interval between adjacent color blood flow image scan lines at the same location is one pulse repetition period.

In one embodiment, when the scanning of a frame of B-mode image is completed, and the scanning of a frame of color blood flow image is not completed yet, any line of a B-mode null scan is used for replacing the B-mode scan until the scanning of the frame of the color blood flow image is completed.

In another aspect, a pulse scanning system is provided, including: a B-mode scanning pulse generating module configured for generating a B-mode scanning pulse; a color blood flow image scanning pulse generating module configured for generating a color blood flow image scanning pulse; and a control module configured for controlling a type, shape, and timing of a transmission pulse and array elements involved in transmission. In one embodiment, the control module is connected to the B-mode scanning pulse generating module and the color blood flow image scanning pulse generating module respectively.

In yet another aspect, a method for simultaneously displaying a blood flow image and a B-mode image is provided includes: scanning an image by using the pulse scanning method to generate a scanning pulse; transmitting the scanning pulse; receiving an ultrasonic echo of the scanning pulse, and converting the received ultrasonic echo into an electric signal; performing wave beam synthesization on the converted electric signal, and separating a B-mode image signal from a color blood flow image signal; processing the B-mode image signal to acquire B-mode image data and processing the color blood flow image signal to acquire color blood flow image data; combining the B-mode image data and the color blood flow image data to form data to be displayed simultaneously; and simultaneously displaying the blood flow image and the B-mode image.

In another aspect, a system for simultaneously displaying a blood flow image and a B-mode image includes a transmission and reception module, an ultrasonic transducer, a beamformer module, a B-mode signal processing module, a color blood flow image signal processing module, a display module, and the pulse scanning system. The pulse scanning system, the transmission and reception module, and the ultrasonic transducer are successively connected to form a transmission circuit; the ultrasonic transducer, the transmission and reception module, and the beamformer module are successively connected; the B-mode signal processing module and the color blood flow image signal processing module are respectively connected to the beamformer module to receive data sent by the beamformer module; and an output end of the B-mode signal processing module and an output end of the color blood flow image signal processing module are connected to the display module.

According to the present disclosure, during ultrasonic color blood flow imaging, imaging is performed by using a continuous blood flow scan based on the technology of multiple wave beams, so as to acquire better blood flow information. In a continuous blood flow scan group (CCgroup) using a pulse repetition period (1/CPRF) of Color scan as a time unit, a part of the time is used for a Color scan, and a part of the time is used for a B-mode scan, so as to save scanning time. A Color scan in a continuous blood flow scan group includes C scan lines in all sampling boxes, and a time interval between adjacent Color scan lines at the same location is 1/CPRF, so that the time interval between the adjacent Color scan lines at the same location is shortened.

Figure 2:
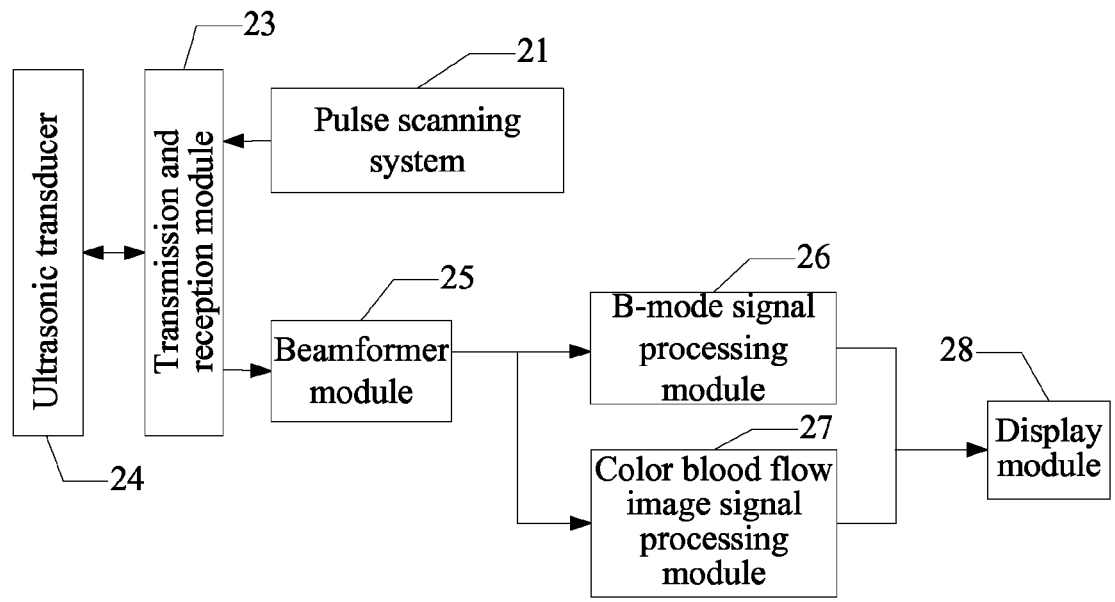
FIG. 2 is a structural block diagram of a device for simultaneously displaying an ultrasonic continuous blood flow image and a B-mode image according to the present disclosure.

FIG. 2 is a block diagram of a device for simultaneously displaying an ultrasonic continuous blood flow image and a B-mode image according to the present disclosure. In one embodiment, a pulse scanning system 21 is pre-configured with a scanning mode and generates a pulse signal. The pulse signal is sent to an ultrasonic transducer 24 through a transmission and reception module 23, and the ultrasonic transducer 24 converts the pulse signal into an ultrasonic signal for transmission. An echo is induced when the ultrasonic signal reaches tissues in human body, and the ultrasonic transducer 24 transfers the received echo to the transmission and reception module 23.

After receiving an echo signal, the transmission and reception module 23 sends the echo signal to a beamformer module 25 for processing to increase a signal to noise ratio of the echo signal. A signal output by the beamformer module 25 is sent to a corresponding signal processing module according to properties of the echo signal. Signals related to a B-mode image are sent to a B-mode signal processing module 26 to acquire two-dimensional B-mode image data. Signals related to a color blood flow image are sent to a Color signal processing module 27 to acquire color blood flow image data. Finally, the B-mode image data and the color blood flow data are combined by a display module 28 to form result data to be simultaneously displayed on a monitor.

Figure 3:
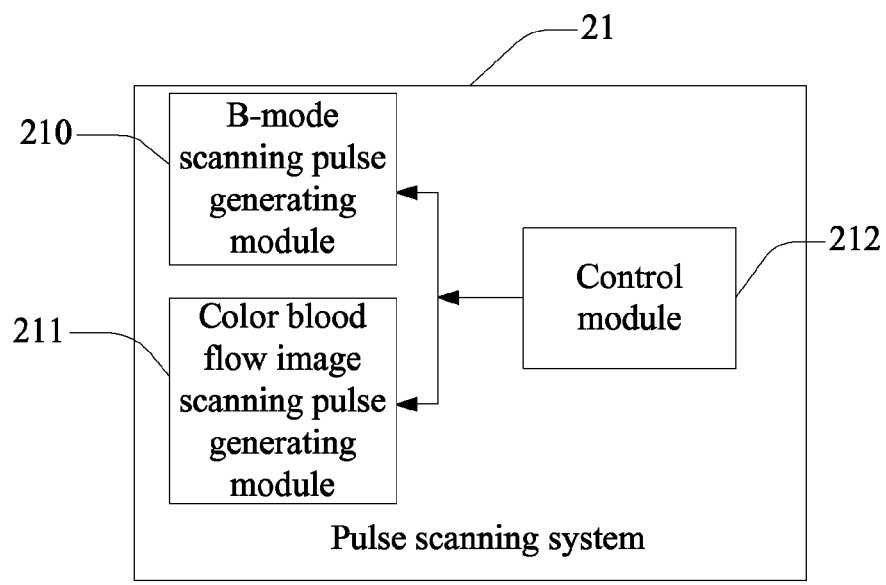
FIG. 3 is a structural block diagram of a pulse scanning system according to the present disclosure.

FIG. 3 is a structural block diagram of the pulse scanning system shown in FIG. 2. In one embodiment, the pulse scanning system 21 includes a B-mode scanning pulse generating module 210, a Color scanning pulse generating module 211, and a control module 212. The B-mode scanning pulse generating module 210 is used for generating a B-mode scanning pulse. The Color scanning pulse generating module 211 is used for generating a Color scanning pulse. The control module 212 is used for controlling a type (that is, controlling the B-mode scanning pulse generating module or the Color scanning pulse generating module), shape, and timing of a transmission pulse and array elements involved in transmission. The control module 212 is connected to the B-mode scanning pulse generating module 210 and the Color scanning pulse generating module 211, respectively.

Figure 4:
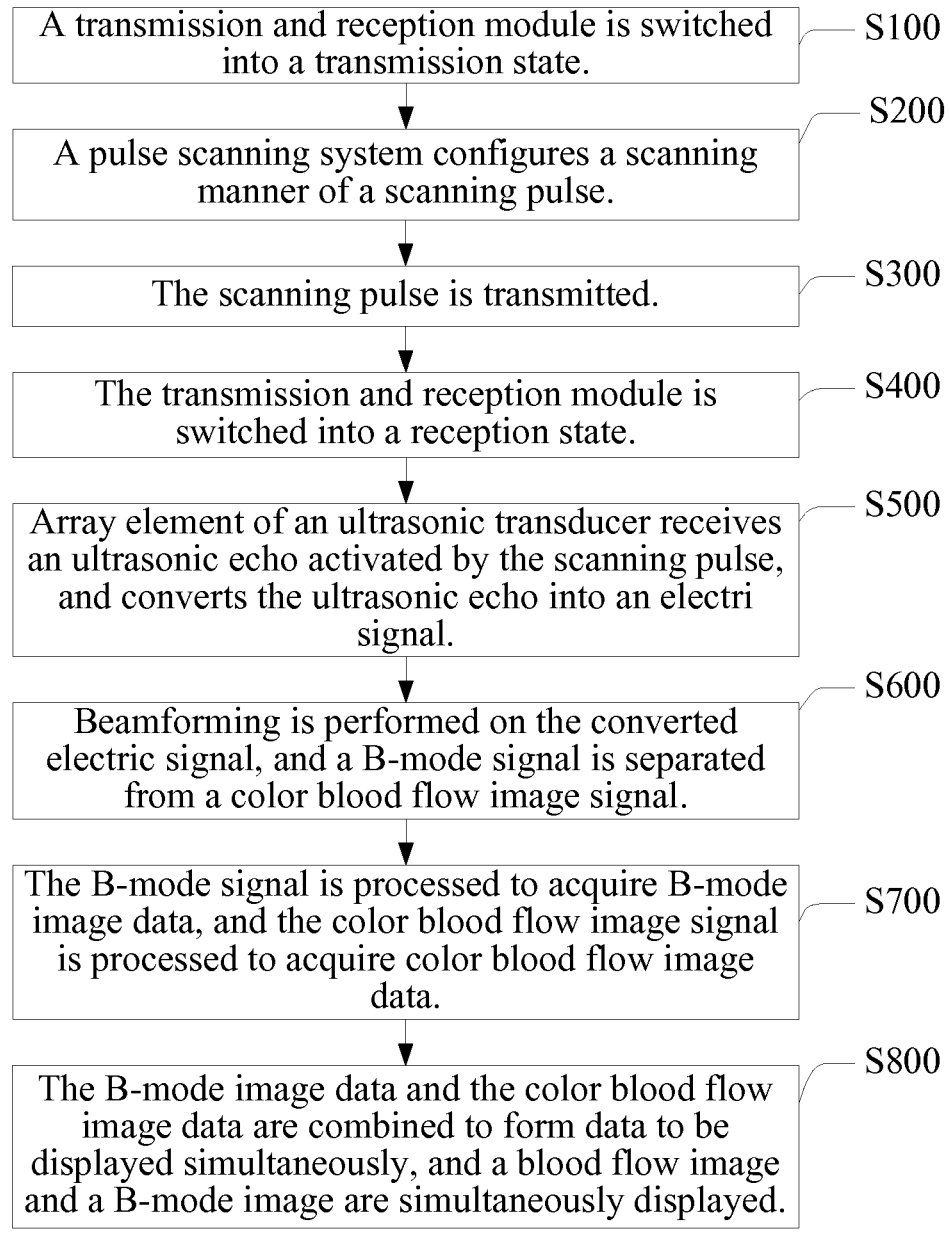
FIG. 4 is a flow chart of a method for simultaneously displaying a continuous blood flow image and a B-mode image according to the present disclosure.

FIG. 4 is a flow chart of a method for simultaneously displaying a continuous blood flow image and a B-mode image according to the present disclosure. Referring to FIG. 4, the method may include the following steps.

In Step S100, a transmission and reception module is switched into a transmission state.

In Step S200, a pulse scanning system configures a scanning method for a scanning pulse, and generates a scanning pulse (specific configuration of the scanning method is described later).

In Step S300, the scanning pulse is transmitted.

When the scanning pulse is transmitted, ultrasound waves are emitted from array elements of an ultrasonic transducer to a human body or other imaging targets.

In Step S400, the transmission and reception module is switched into a reception state.

In Step S500, each array element of an ultrasonic transducer receives an ultrasonic echo activated by the scanning pulse, and converts the ultrasonic echo into an electric signal.

In Step S600, beamforming is performed on the converted electric signal, and a B-mode signal is separated from a Color signal.

In Step S700, the B-mode signal is processed through a B-mode signal processing module to acquire B-mode image data, and the Color signal is processed through a Color signal processing module to acquire color blood flow image data.

In Step S800, the B-mode image data and the color blood flow image data are combined to form data to be displayed simultaneously, and a blood flow image and a B-mode image are simultaneously displayed.

Figure 5:
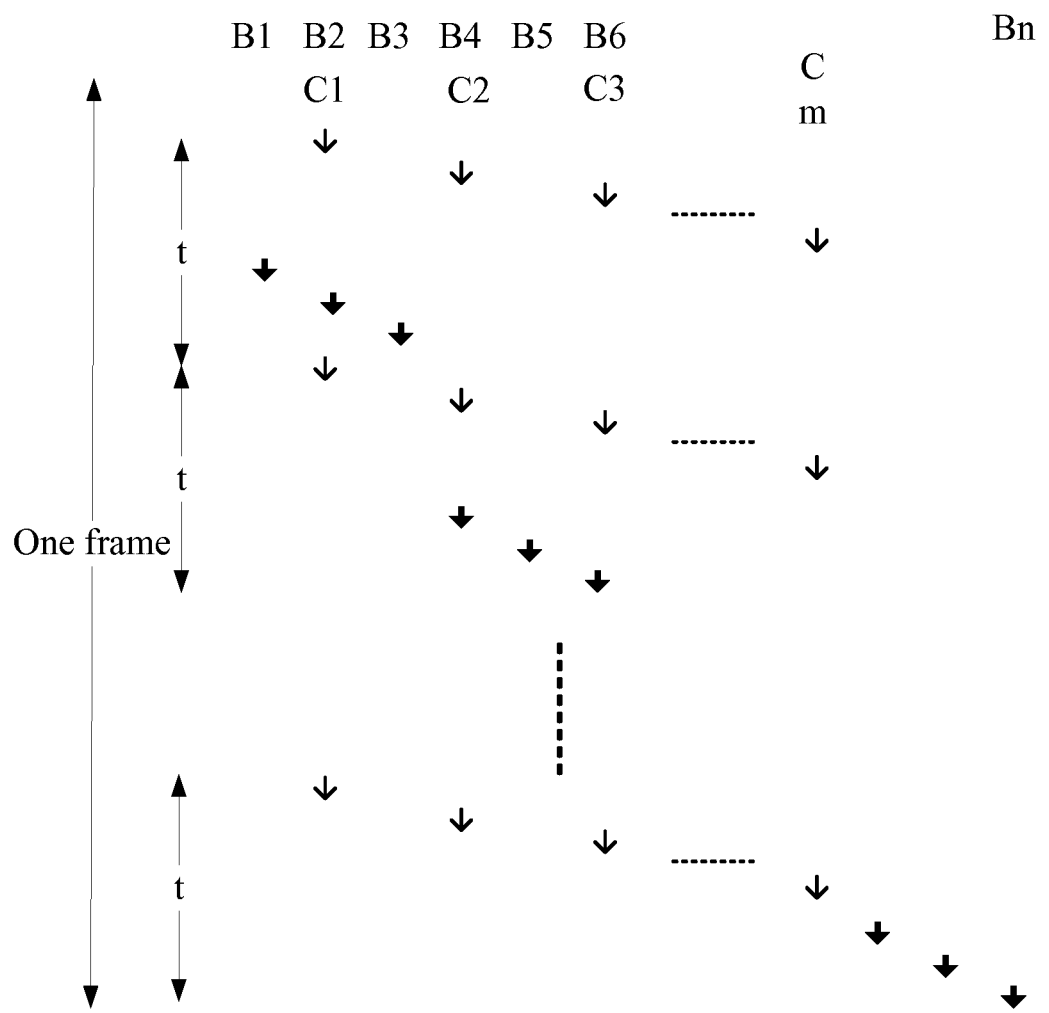
FIG. 5 is a schematic view of scanning according to the present disclosure.

FIG. 5 is a schematic view of a scanning method for simultaneously displaying a continuous blood flow image and a B-mode image according to the present disclosure. In one embodiment, a pulse scanning method may include completing scanning of an entire color blood flow image through an interleave-scan packet. An interleave-scan packet includes at least one continuous blood flow scan group. The continuous blood flow scan group uses a pulse repetition period of the color blood flow image scanning as a unit scanning time. Within each unit scanning time, a part of the time is used for the color blood flow image scanning and a part of the time is used for scanning of a B-mode image. Each of the continuous blood flow scan groups includes a group of complete Color scan lines (C1, C2, . . . , Cm) and at least one B-mode scan line. The B-mode scan lines in each of the interleave-scan packets form a frame of complete B-mode scan lines (B1, B2, . . . Bn), and a group of Color scan lines in each of the interleave-scan packets form a frame of complete Color scan lines.

In the continuous blood flow mode, the system can achieve a considerable scan range and horizontal resolution capability by the method for multiple reception of wave beams on the basis of the reduced number of the transmission lines. Therefore, when the pulse repetition frequency of the B-mode scan is low, the scanning of the entire color blood flow image can be completed through one interleave-scan packet. The system uses a pulse repetition period t of the Color scan as a scan unit, all Color scan is completed first, and then the remaining time is used for completing several iterations of the B-mode image scan. The scan unit of the period t is defined as a continuous blood flow scan group (a CCgroup), and after several CCgroups, the scanning of a frame of a B-mode image is achieved. When the frame of the B-mode image is scanned, the process is repeated to realize the simultaneous display of the continuous blood flow image and the B-mode image.

The pulse repetition frequency CPRF of the Color scan is determined by a maximal value of a speed measuring range S selected by a user, the speed C of sound, and current transmission frequency f. A formula for calculating the pulse repetition frequency can be:

$$CPRF=4f*S/C.$$

Therefore, a formula for calculating the pulse repetition period t is:

$$t=C/(4f*S).$$

Assuming that a remote end depth of a Color sampling window is D (referring to FIG. 7), a minimal time T1 for completing a Color scan can be:

$$T1=(2*D/C).$$

Likewise, assuming that a maximal depth of B is d (referring to FIG. 7), a minimal time T2 for completing a B-mode scan can be:

$$T2=(2*d/C).$$

In view of the above, the scanning is performed with the CCgroup being one group, and the Color scan is performed first. When the Color scan is completed, the remaining time is used for performing the B-mode scan, and the B-mode scan line varies as the CCgroup changes. Therefore, a time interval between adjacent color blood flow image Color scan lines at the same location can be one pulse repetition period. In this embodiment, a first CCgroup can include B-mode scan lines B1, B2, and B3; a second CCgroup can include B-mode scan lines B4, B5, and B6; and, accordingly, the last scanned scan line is Bn. The number of the B-mode scan lines in each of the CCgroups varies as the parameter, such as the CPRF, changes.

When the times of the repetition scan of the Color signal is N, the number M of the B-mode scan that can be performed in each of the CCgroups satisfies:

$$M=\text{floor}[(t-N*T1)/T2].$$

In the formula, floor is a round-down function to ensure that M is an integer, e.g., floor(3.1)=3, and floor(4.9)=4.

Figure 6:
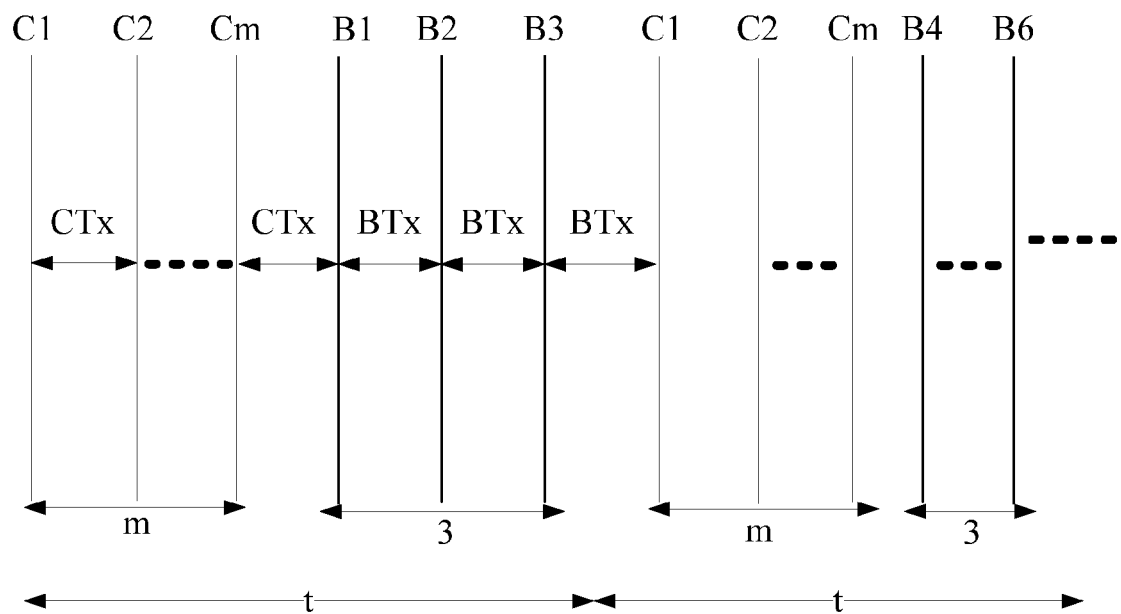
FIG. 6 is a schematic view of specific scanning time intervals between scan lines according to the present disclosure.

Referring to FIG. 6, an example of a scan relation in the scanning method in FIG. 5 is provided. An interval between the Color scan and the Color scan is CTx, an interval between the Color scan and the B scan is CTx, an interval between the B-mode scan and the B-mode scan is BTx, and an interval between the B-mode scan and the Color scan is BTx, in which:

$$CTx=T1; \text{ and}$$

$$BTx=[(t-N*CTx)/M].$$

In addition, a scanning time interval of the system may be defined according to actual needs. After the system completes a frame of B-mode scan, if a frame of Color scan is not completed yet, any line of a B-mode null scan (for example, the last line of B-mode null scan, that is, the scan of B-mode n) can be used for replacing the B-mode scan until the scanning of the frame C is completed, so as to guarantee that the interval of the Color scan does not change.

Figure 7:
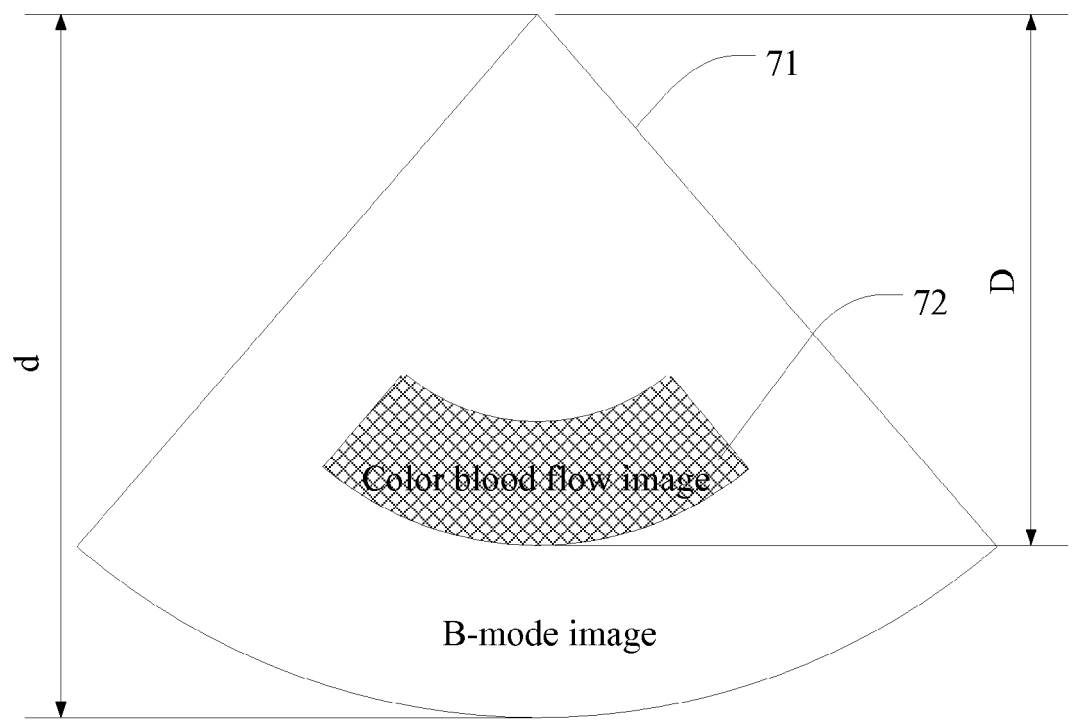
FIG. 7 is a schematic view of simultaneously displaying an ultrasonic continuous blood flow image and a B-mode image according to the present disclosure.

FIG. 7 is a schematic view of simultaneously displaying an ultrasonic continuous blood flow image and a B-mode image according to the present disclosure. In the depicted embodiment, the fan-shaped area is a B-mode image display area 71, and a shaded area at the center of the B-mode image is a color blood flow image display area 72. During actual image display, the B-mode image display area displays a two-dimensional grayscale image of tested human tissues, and the color blood flow image display area displays a blood flow image formed by color coding.

Therefore, according to scan control methods in the present disclosure, the B-mode signal processing and the Color signal processing can be respectively performed on the received echo, so that during continuous blood flow imaging, the method for simultaneously displaying the Color image and the B-mode image can be implemented.

In one embodiment, each scanning time interval is enlarged to compensate for effects due to factors, such as the switching of the system between transmission and reception, the scanning of the B-mode image may be performed first, and then the scanning of the Color image is performed.

While specific embodiments and applications of various methods and systems have been illustrated and described, it is to be understood that the invention claimed hereinafter is not limited to the precise configuration and components disclosed. Various modifications, changes, and variations apparent to those of skill in the art may be made in the arrangement, operation, and details of the methods and systems disclosed.

Furthermore, the methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified without departing from the scope of the invention as claimed.

The embodiments disclosed may include various steps, which may be embodied in machine-executable instructions to be executed by a general-purpose or special-purpose computer (or other electronic device). Alternatively, the steps may be performed by hardware components that contain specific logic for performing the steps, or by any combination of hardware, software, and/or firmware.

Embodiments of the present invention may also be provided as a computer program product including a non-transitory computer-readable medium having stored thereon instructions that may be used to program a computer (or other electronic device) to perform processes described herein. The computer-readable medium may include, but is not limited to, floppy diskettes, optical disks, CD-ROMs, DVD-ROMs, ROMs, RAMs, EPROMs, EEPROMs, magnetic or optical cards, or other type of media suitable for storing electronic instructions.

Those of skill in the art will appreciate that the various illustrative logical blocks, modules, circuits, and algorithm steps described in connection with the embodiments disclosed herein may be implemented as electronic hardware, computer software, or combinations of both. To illustrate the interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the invention as claimed hereinafter.

What is claimed is:

1. A pulse scanning method, the method comprising:
   scanning a plurality of scan groups within an interleave-scan packet, wherein scanning each scan group of the plurality of scan groups comprises,
      scanning a plurality of color blood flow image scan lines, wherein the plurality of color blood flow image scan lines comprise all color blood flow image scan lines for forming a frame of color blood flow image, and
      scanning at least one B-mode scan line for a B-mode image,
      wherein scanning each scan group of the plurality of scan groups is performed within a pulse repetition period of the color blood flow image scanning,
   wherein the plurality of scan groups within the interleave-scan packet together comprises all B-mode scan lines for forming a frame of B-mode image,
   wherein the method further comprising calculating the pulse repetition period using a formula:

$$t = C/(4f*S),$$

wherein t is the pulse repetition period, C is a speed of sound, f is current transmission frequency, and S is a maximal value of a speed test range selected by a user.

2. The pulse scanning method according to claim 1, wherein:
   scanning each scan line of the plurality of color blood flow image scan lines comprises a duration of at least time T1, which satisfies T1=(2*D/C), wherein D is a remote end depth of a color blood flow image sampling window, and C is the speed of sound; and
   scanning each scan line of the B-mode scan lines comprises a duration of at least time T2, which satisfies T2=(2*d/C), wherein d is a maximal depth of the B-mode image, and C is the speed of sound.

3. The pulse scanning method according to claim 2, further comprising calculating a number M of the B-mode scan lines in each of the scan groups using a formula:

$$M = \text{floor}[(t - N*T1)/T2],$$

wherein M is the number of the B-mode scan lines, t is the pulse repetition period, N is the times of the repetition scan of the color blood flow image scan lines in one scan group, T1 is the minimum time required for completing each color blood flow image scanning, T2 is the minimum time required for completing each B-mode scan, and floor is a round-down function.

4. The pulse scanning method according to claim 3, wherein scanning the plurality of scan groups comprises scanning the plurality of scan groups such that a time interval between a color blood flow image scan line followed by a color blood flow image scan line is CTx, a time interval between a color blood flow image scan line followed by a B-mode scan line is CTx, a time interval between a B-mode scan line followed by a B-mode scan line is BTx, and a time interval between a B-mode scan line followed by color blood flow image scan line is BTx, wherein $$CTx = T1; \text{ and}$$

$$BTx = [(t - N*CTx)/M].$$

* * * * *